United States Patent [19]

Gordon

[11] Patent Number: 5,026,392
[45] Date of Patent: Jun. 25, 1991

[54] PROSTHETIC EYE

[76] Inventor: Gregg E. Gordon, 3 Sadore La., Apt. 6T, Yonkers, N.Y. 10710

[21] Appl. No.: 525,819

[22] Filed: May 21, 1990

[51] Int. Cl.$^5$ .............................................. A61F 2/14
[52] U.S. Cl. ..................................................... 623/4
[58] Field of Search ......................................... 623/4

[56] References Cited

U.S. PATENT DOCUMENTS

| | | | |
|---|---|---|---|
| 1,268,885 | 6/1918 | Sampson | 623/4 |
| 1,633,986 | 6/1927 | Greiner | 623/4 |
| 2,322,117 | 6/1943 | Dimitry | 623/4 |
| 2,466,780 | 4/1949 | Radin | 623/4 |
| 2,467,401 | 4/1949 | Murphy et al. | 623/4 |
| 2,497,873 | 2/1950 | Erpf | 623/4 |
| 2,516,804 | 7/1950 | Rolf et al. | 623/4 |
| 2,551,781 | 2/1951 | Yuhas | 623/4 |
| 2,563,462 | 8/1951 | Galeski | 623/4 |
| 2,571,721 | 10/1951 | Jardon | 623/4 |
| 2,572,416 | 10/1951 | Wilson | 623/4 |
| 2,574,750 | 11/1951 | Moore | 623/4 |
| 2,580,583 | 1/1952 | Noelle | 623/4 |
| 2,593,150 | 4/1952 | Jardon | 623/4 |
| 2,603,791 | 7/1952 | Jardon et al. | 623/4 |
| 2,603,792 | 7/1952 | Jardon et al. | 623/4 |
| 2,617,994 | 11/1952 | Noelle | 623/4 |
| 2,629,877 | 3/1953 | Jardon | 623/4 |
| 2,634,423 | 4/1953 | Clarke | 623/4 |
| 2,635,290 | 4/1953 | Yuhas . | |
| 2,637,043 | 5/1953 | Morrell | 623/4 |
| 2,643,392 | 6/1953 | Busch | 623/4 |
| 2,649,590 | 8/1953 | Cutler | 623/4 |
| 2,653,327 | 9/1953 | Allen et al. | 623/4 |
| 2,653,328 | 9/1953 | Anderson et al. | 623/4 |
| 2,660,732 | 12/1953 | Stone | 623/4 |
| 2,661,480 | 12/1953 | Rosen et al. | 623/4 |
| 2,667,645 | 2/1954 | Moulton | 623/4 |
| 2,673,984 | 4/1954 | Clarke | 623/4 |
| 2,675,561 | 4/1954 | Clarke | 623/4 |
| 2,692,391 | 10/1954 | Gougelman | 623/4 |
| 2,792,573 | 5/1957 | Clark et al. | 623/4 |
| 2,810,134 | 10/1957 | Radin | 623/4 |
| 2,817,845 | 12/1957 | Clarke | 623/4 |
| 3,070,808 | 1/1963 | Allen | 623/4 |
| 3,364,501 | 1/1968 | Stafford | 623/4 |
| 4,731,077 | 3/1988 | Allen | 623/4 |

Primary Examiner—Randy Citrin Shay
Attorney, Agent, or Firm—Blum Kaplan

[57] ABSTRACT

A prosthetic eye for use in replacing the natural eye of a user in an eye cavity having eye muscles. The prosthetic eye has a spherical body in the shape and form of the natural eye. The spherical body is provided with several receiving regions extending radially from the anterior section of the eye. Further, the prosthetic eye has tabs for attaching to the eye muscles. The tabs with the attached eye muscles are inserted into the receiving regions to couple the muscles to the prosthetic eye. The tabs may be adjusted by removing and reinserting the tabs from the receiving regions and repositioning them in the appropriate location in the region so that the prosthetic eye may rest in its natural position in the cavity with respect to the remaining natural eye.

35 Claims, 4 Drawing Sheets

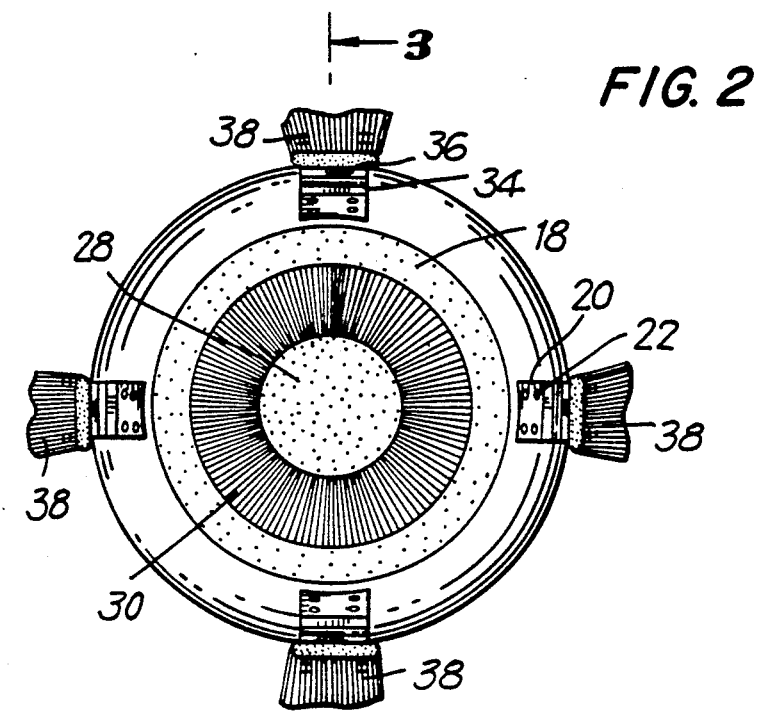
FIG. 2
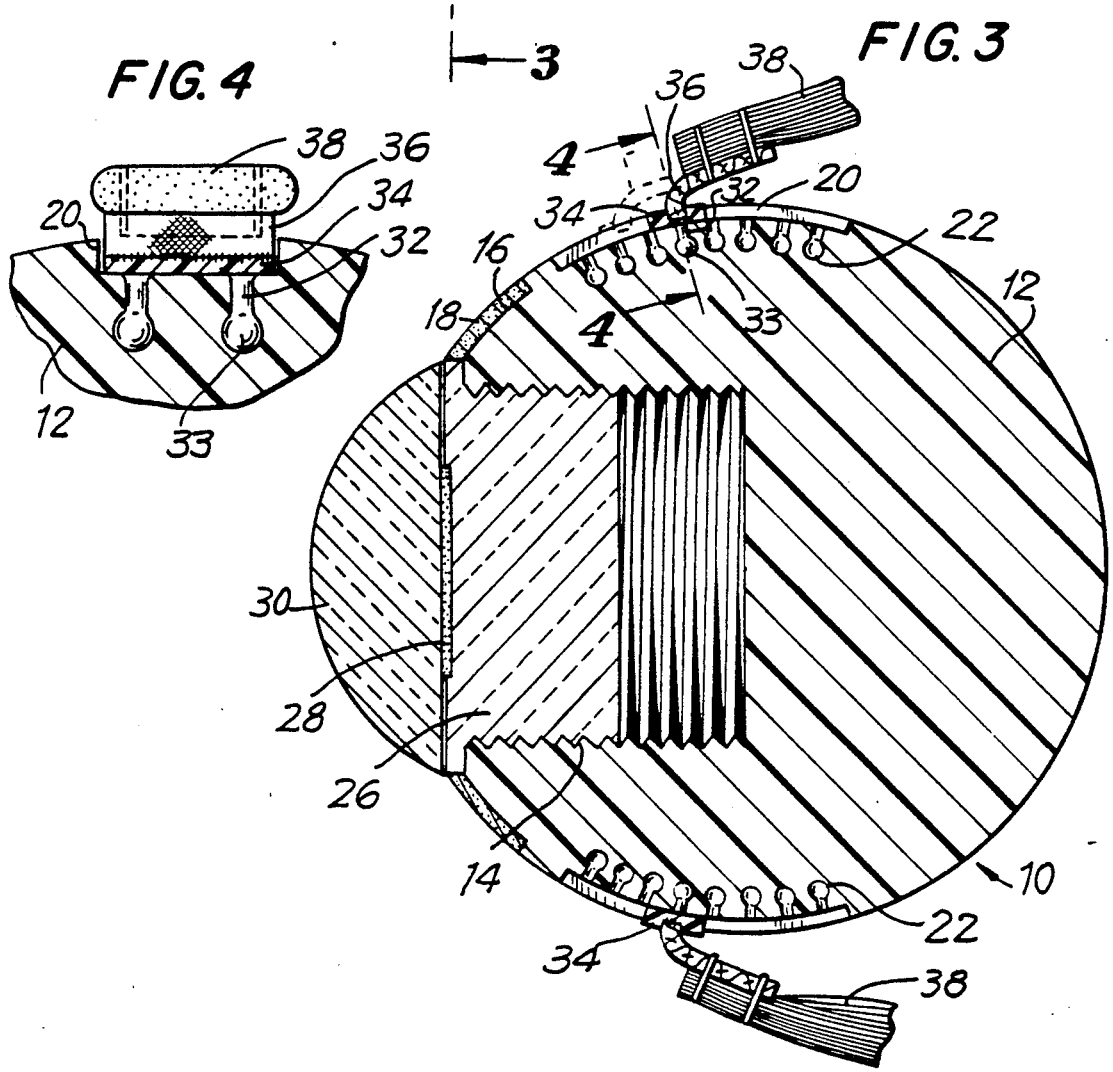
FIG. 4
FIG. 3

PROSTHETIC EYE

BACKGROUND OF THE INVENTION

This invention relates generally to a prosthetic eye, and, in particular, to a prosthetic eye that provides a direct adjustable coupling between the severed extra-ocular muscles and the prosthetic eye. The prosthetic eye is constructed of a bio-compatible material and further allows for a cosmetically acceptable appearance in the immediate post-operative period.

To date, the prior art reveals many flaws in the construction and insertion of a prosthetic eye. The failures are related but not limited to complications of extrusion of the prosthesis from the orbital tissue as well as potentially fatal orbital infections.

Problems arise due to poor bio-compatibility of the materials used to secure the prosthesis to the tissue surrounding the eye. A variety of materials and devices have been used including prongs, clamps, meshes, and filaments of gold, tantalum, vitallium, and plastic, but are less than completely satisfactory due to the lack of ingrowth between the tissue and that of the foreign material. The poor bio-compatibility of these materials has resulted in loosening of the prosthesis with mechanical erosion of the surrounding tissue causing orbital infection and extrusion of the prosthesis.

In addition, the prior art has obtained poor results due to the lack of an effective method of attaching the conjunctiva to the prosthesis. The implant of a prosthetic eye is a foreign body and therefore its presence increases the risk of orbital infection following surgical implantation. Accordingly, it is necessary to protect the orbital tissues from the ingress of microorganisms by closing the conjunctiva over the implant so that a water-tight seal can be achieved. The prior art has revealed flawed techniques in creating a water-tight seal including purse-string sutures, anchoring the conjunctiva to metallic meshes, and suturing the conjunctiva to itself after passing it through apertures in the prosthesis. However, in all these cases, a gap persisted at the interface of the implant and conjunctiva, resulting in an increased incidence of infection.

Furthermore, the prior art has failed to properly design an implant with the biomechanics to control the eye in a more natural appearing way. In order to achieve the most natural appearing ocular motility, the muscles must be attached to the prosthesis in their anatomic position. Further, to accomplish this goal, the prosthesis must possess a size and shape similar to that of the natural eye. The prior art fails to recreate normal biomechanics necessary to create a more natural appearing prosthetic eye.

Presently, the most accepted technique for the replacement of a diseased natural eye is to remove the eye, suture the remaining extra-ocular muscles over a plastic or glass sphere and then close the conjunctiva and Tenon's membrane over the muscles. After a period of healing, the patient is then measured for a separate cosmetic prosthesis and must further endure several weeks without an eye while the actual construction and art work of the prosthesis is completed. The patient, who has already undergone the trauma of losing an eye, must then be subjected to the additional stress of spending one to two months in a cosmetically unacceptable state.

Further, as discussed above, once inserted, the motility of the cosmetic prosthesis is quite poor due to the absence of any direct connection between the extra-ocular muscles and the prosthesis. Hence, the prosthesis tends to move in a manner that is poorly coordinated with that of the patient's other natural eye giving the patient the appearance of being cross-eyed or wall-eyed. The prior art has failed to provide a prosthetic eye that allows for a cosmetically acceptable appearance in the immediate post-operative period. Additionally, the insertion methods of the prior art have neglected the use of an adjusting prosthetic eye to enable the patient to have a more natural appearing eye.

Accordingly, it is desired to provide a prosthetic eye which is constructed of a bio-compatible material, has an effective method of attaching the conjunctiva to the prosthesis, has the necessary biomechanics to control the prosthetic eye movement and adjust the location of the eye in a natural appearing manner, and a safe and early surgical method of implantation.

SUMMARY OF THE INVENTION

Generally speaking, in accordance with the present invention, a prosthetic eye for use in replacing the natural eye of a user in an eye cavity with eye muscles is provided. The prosthetic eye includes a spherical body in the shape and form of a natural eye. The spherical body is provided with several receiving regions extending radially from the anterior section of the eye. Further, the prosthetic eye includes tabs to couple to the eye muscles. The tabs with the attached eye muscles are inserted into the receiving regions to connect the muscles to the prosthetic eye. The tabs may be adjusted by removing and reinserting the tabs from the receiving regions and repositioning them in the appropriate location in the receiving region so that the prosthetic eye may rest in its natural position in the cavity with respect to the remaining natural eye.

Accordingly, it is an object of the present invention to provide an improved prosthetic eye for insertion into an eye cavity.

Another object of the present invention is to provide a prosthetic eye that may be secured to the extra-ocular muscles and the conjunctiva with a unique bio-compatible interface.

Yet another object of the present invention is to provide a prosthetic eye that allows for the adjustment of the muscle tension of the prosthetic eye and the overall prosthesis alignment with the remaining natural eye.

Still another object of the invention is to provide a prosthetic eye that enables immediate post operative psychological benefits to the patient by avoiding the delay and traumatic period between surger and the final fitting of the prosthesis.

Yet still another object of the present invention is to provide prosthetic eye with a water tight seal between the conjunctiva and the prosthesis to act as a barrier to infection.

Still other objects and advantages of the invention will in part be obvious and will in part be apparent from the specification.

The invention accordingly comprises the several steps and the relation of one or more of such steps with respect to each of the others, and the article possessing the features, properties, and the relation of elements, which are exemplified in the following detailed disclosure, and the scope of the invention will be indicated in the claims.

BRIEF DESCRIPTION OF THE DRAWING

For a fuller understanding of the invention, reference is had to the following description taken in connection with the accompanying drawings, in which:

FIG. 2 is a front plan view of the prosthetic eye depicted in FIG. 1;

FIG. 3 is an enlarged sectional view taken along line 3—3 of FIG. 2;

FIG. 4 is an enlarged sectional view taken along line 4—4 of FIG. 3

DETAILED DESCRIPTION OF THE PREFERRED EMBODIMENTS

Figure 1:
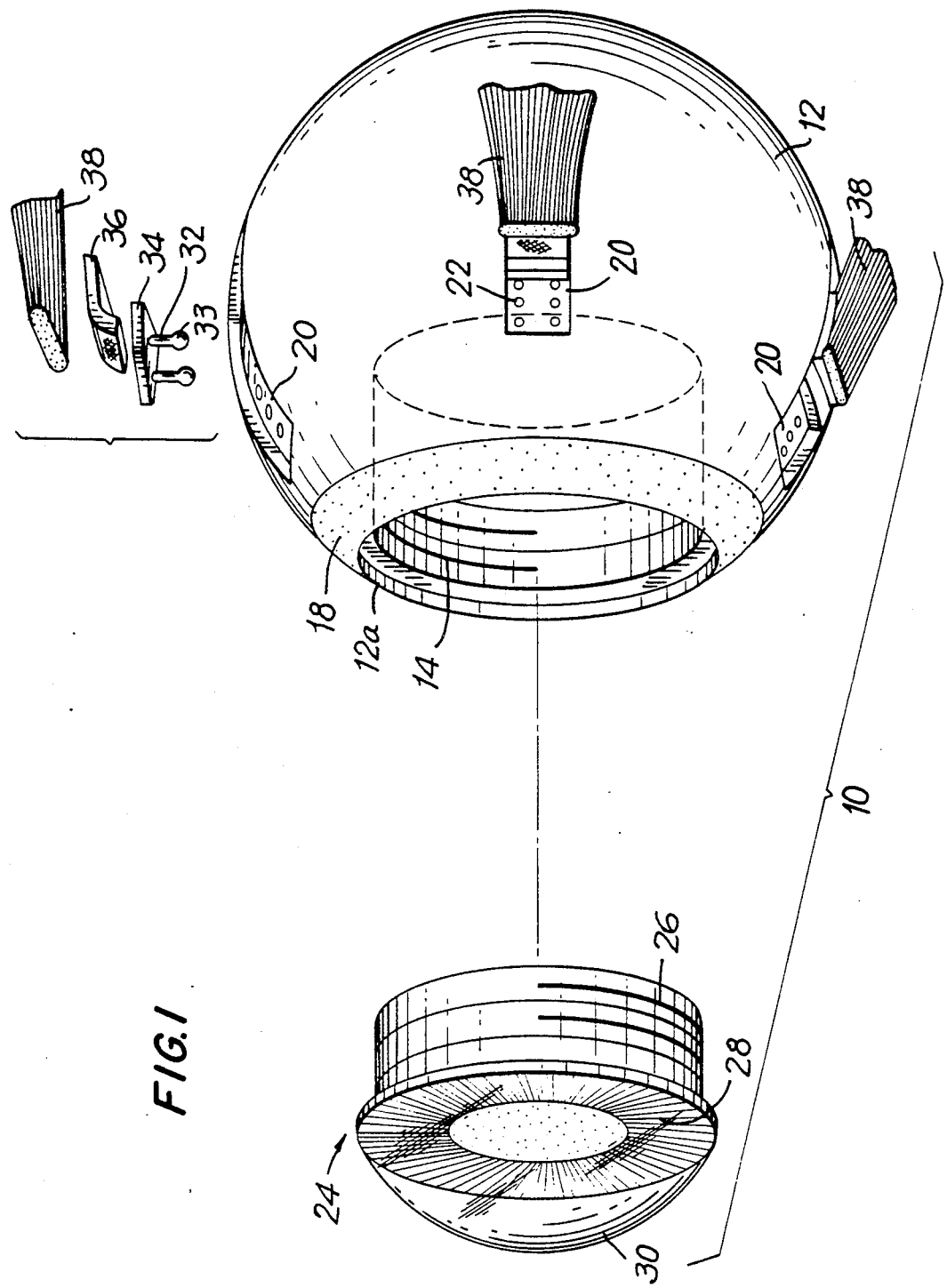
FIG. 1 is an exploded perspective view of a prosthetic eye constructed in accordance with a preferred embodiment of the present invention.

Reference is first made to FIGS. 1 through 3 of the drawings which depict a prosthetic eye, generally indicated at 10, and constructed in accordance with a preferred embodiment of the present invention. Prosthetic eye 10 includes a scleral portion 12 and a removable anterior segment assembly 24. Scleral portion 12 is preferably manufactured from an inert bio-compatible material such as polymethylmethacrylate or silicone manufactured by injection-molding techniques. Scleral portion 12 includes a central recess or blind opening 14 molded into front surface 12a of scleral portion 12 for receiving anterior segment assembly 24. A conjunctival anchor cuff 18 surrounds central recess 14 and is constructed of a bio-compatible material which allows for in-growth of the conjunctiva to form a water-tight connection.

Conjunctival anchor cuff 18 is supported in an annular recess 16 surrounding central recess 14. In the preferred embodiment, conjunctival anchor cuff 18 is constructed of a porous expanded PTFE (e.g., polytetrafluoroethylene) or porous Dacron. Conjunctival anchor cuff 18 is further secured to scleral portion 12 by use of adhesive agents (e.g., cyanoacrylate) to bond conjunctival anchor cuff 18 in recess 16. Scleral portion 12 is further provided with four grooved recesses 20 which are oriented radially from central recess 14. The positions of grooved recesses 20 correspond to the positions of extra-ocular or rectus muscles 38 in the eye cavity. Grooved recesses 20 are provided with spaced pairs of openings 22 for selectively receiving prongs connected to extra-ocular muscles 38 as described below in detail.

Anterior segment assembly 24 includes a translucent cylindrical body 26, a pigmented iris 28 and a translucent cornea 30. Pigmented iris 28 is provided with a textured surface similar to the natural iris and is molded of an inert material (e.g. polymethylmethacrylate). Pigmented iris 28 is painted to resemble the pigmentation of the natural eye. In an alternative embodiment, a photograph of the natural iris may be used to recreate an image of pigmented iris 28 by inserting the photograph into anterior segment assembly 24 in the region of the iris. Translucent cornea 30 and translucent cylinder 26 are then molded around pigmented iris 28 using a translucent material (e.g. polymethylmethacrylate). Translucent cornea 30 may be coated with a thin film of polytetrafluoroethylene material. This will allow the conjunctival or similar epithelial cells to grow on the cornea surface and further enhance biocompatability. Black pigment may then be applied to the outside region of translucent cylinder 26 to give the eye a more natural appearance. Anterior segment assembly 24 would create a natural appearing eye by allowing light to enter the translucent cornea 30 and pupil in a normal fashion. This arrangement allows the light to enter translucent cylinder 26 and be absorbed by the blackened pigmented layer surrounding it.

In this fashion, the construction creates an appearance of depth associated with the natural eye. Anterior segment assembly 24 is then inserted into scleral portion 12 by threading the anterior segment assembly 24 into scleral portion 12 wherein the threading is milled into central recess 14. In an alternative embodiment, anterior segment assembly 24 may be attached to scleral portion 12 by friction created between the two members.

Muscle anchor plate 34, constructed of a flat solid material (e.g. polymethylmethacrylate), includes prongs 32 with flared ends 33. Further, muscle anchor plate 34 is provided with a recess for insertion of muscle tab 36 constructed of a flat porous material (e.g. Dacron or expanded PTFE). Upon insertion, muscle anchor plate 34 integrally attaches to muscle tab 36 by means of an adhesive agent. Extra-ocular muscles 38 are then sutured to muscle tabs 36 connecting anchor plate 34 to the natural eye muscles. In addition to the extra-ocular muscles, the superior and inferior oblique muscles may be attached to the tabs for a more natural connection to the prosthetic eye. In a further alternative embodiment, muscle tabs 36 may be constructed of a Dacron sleeve so that the extra-ocular muscle 38 may be inserted into the sleeve and sutured thereon. Hence, the muscle may become uniquely attached to the muscle anchor plate so that the three components act as one.

Prongs 32 with flared heads 33 are then inserted into one of the pair of openings 22 as clearly shown in FIG. 4. Openings 22 are mirror images of prongs 32 with flared ends 33 so that upon insertion, the two create a tight frictional fit. When anchor prongs 32 are mated in openings 22, muscle anchor plate 34 resting in grooved recess 20 lies flush with the outer surface of scleral portion 12.

Figure 5:
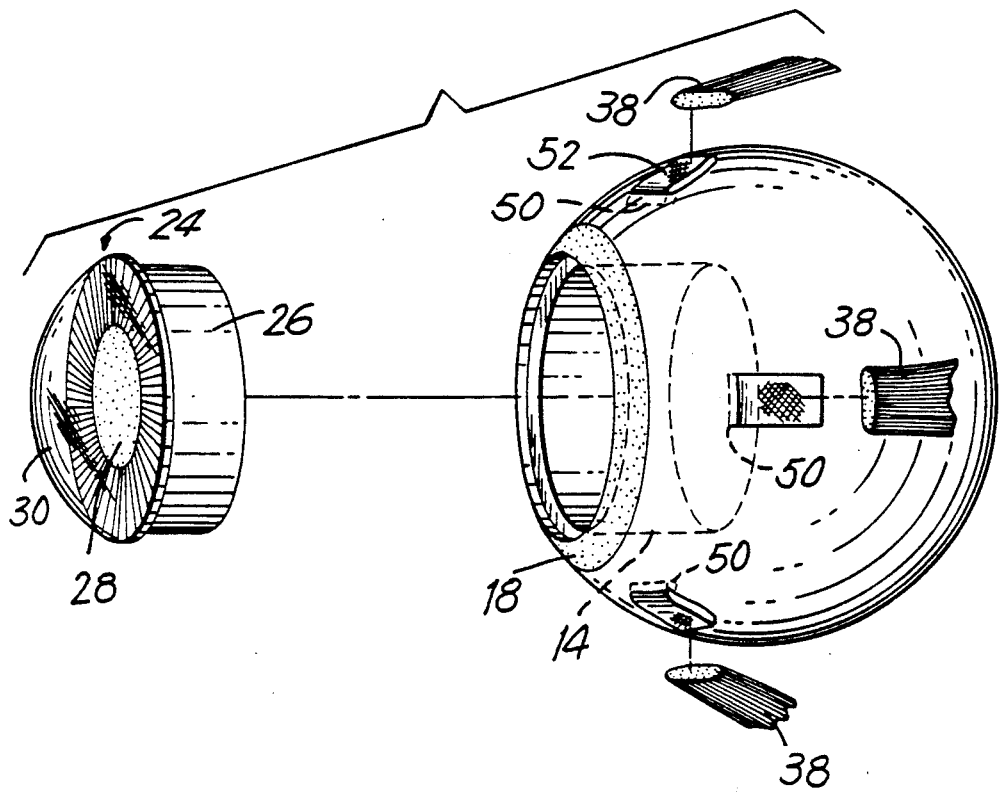
FIG. 5 is an exploded perspective view of a prosthetic eye constructed in accordance with an alternative embodiment of the present invention.
Figure 6:
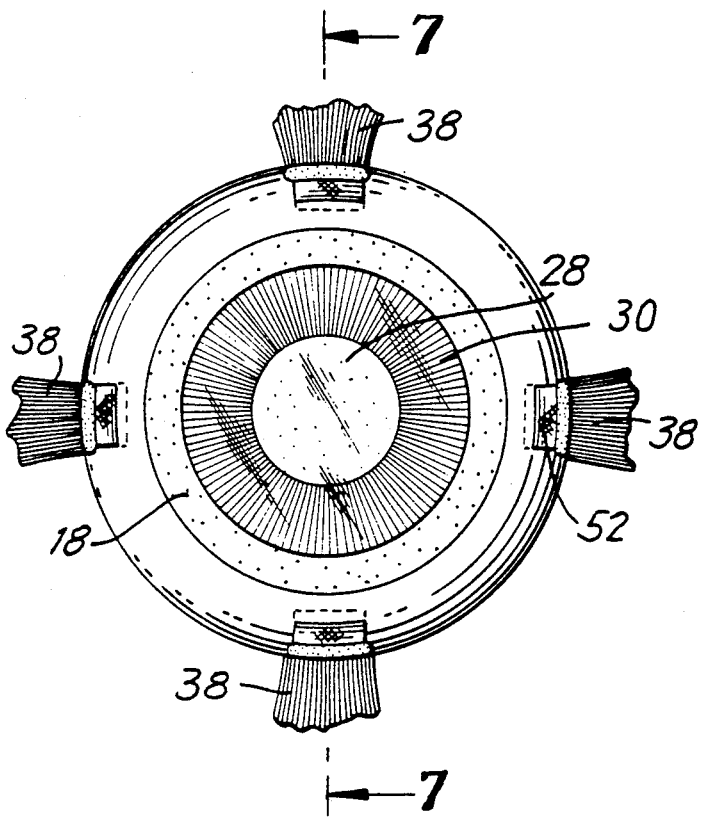
FIG. 6 is a front plan view of the prosthetic eye depicted in FIG. 5.
Figure 7:
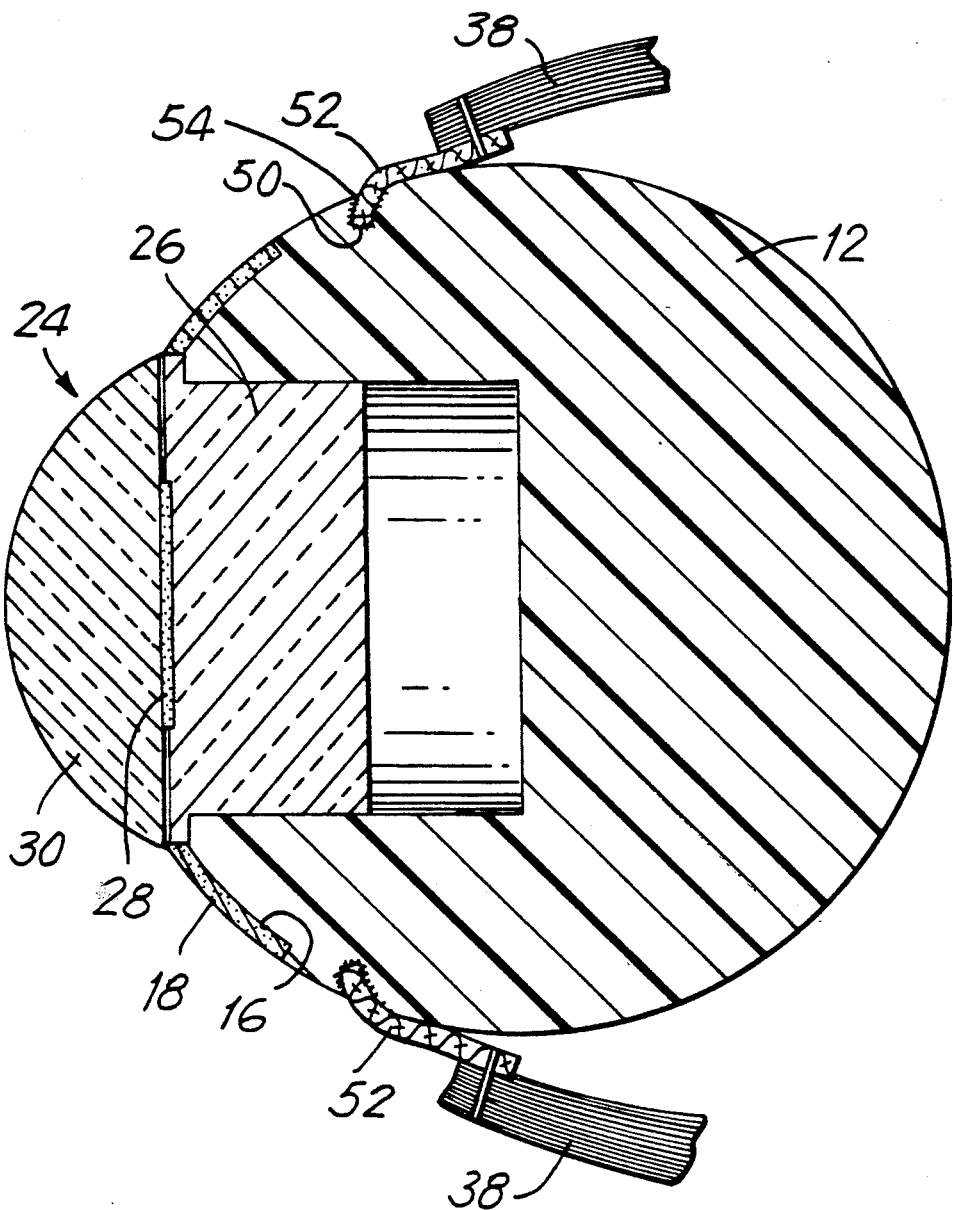
FIG. 7 is an enlarged sectional view taken along line 7—7 of FIG. 5.

Referring now specifically to FIGS. 5 through 7 of the drawings, an alternative embodiment of the invention is shown wherein the anterior segment assembly 24 and the scleral portion 12 are identical to those disclosed above except to the extent of including grooved recesses 20, muscle anchor plate 34 and muscle tabs 36. In the prosthetic eye assembly disclosed in FIGS. 5-7, scleral portion 12 includes four recessed slots 50 oriented radially from central recess 14 corresponding to the position of the extraocular muscles 38. Recessed slots 50 receive a muscle anchor tab 52 which is constructed of a flat porous material (e.g. expanded PTFE or Dacron). Muscle anchor tabs 52 are coupled to recessed slots 50 by means of an adhesive agent. Extraocular muscles 38 are then attached to muscle tabs 52 by suturing.

To insert prosthetic eye 10 of the invention, the patient's diseased natural eye is removed by conventional surgical techniques. Preserving as much of the conjunctiva as possible, the conjunctiva is incised for 360° after which the conjunctiva and Tenon's membrane are dissected from the eye. The extra-ocular muscles and optic nerve are then severed from the eye and the eye is removed. The prosthetic eye is placed within the cone formed by the rectus muscles.

Referring to the embodiment as disclosed is FIGS. 1-4, the extra-ocular muscles 38 are sutured to muscle tabs 36 by utilizing non-absorbable sutures. Additionally, the superior and inferior oblique muscles may be attached to muscle tabs 36 for a more natural connection. To ensure maximal muscle to prosthesis adhesion, the suturing is performed so that extra-ocular muscles 38 completely cover the outer surface of muscle tabs 36. After the four muscles are secured to muscle tabs 36, prongs 32 with flared ends 33 are inserted into selective openings 22 of grooved recesses 20. At this point, the position of prosthetic eye 10 is compared with that of the patient's remaining natural eye. If the prosthetic eye 10 does not appear to be aligned with the natural eye, the muscles may be repositioned by lifting the muscle anchor plates 34. By lifting anchor plates 34, prongs 32 will disengage with the originally selected openings 22 of scleral portion 12 allowing a new muscle attachment position to be selected. After natural eye alignment is achieved, the conjunctiva and Tenon's membrane are sutured to the conjunctiva anchor cuff 18 creating a water-tight seal. An absorbable suture (e.g. 8-0 vicryl) is utilized to position these membranes in their natural anatomic position.

Realignment of the prosthetic eye may become necessary even though the eye was properly aligned at the time of surgery. This is a result of post-operative scarring or atrophy of the orbital tissues. If the misalignment is found to be cosmetically significant, then a re-alignment may be achieved by a second procedure. This procedure may be safely performed without general anesthesia utilizing only topically applied anesthetic drops. The conjunctiva and Tenon's membrane are dissected from the conjunctival anchor cuff 18. As with the alignment during the first procedure, muscle anchor plates 34 are removed from openings 22 of scleral portion 12. Prongs 32 are then inserted into the appropriate pair of openings 22 to properly realign the prosthetic eye. The conjunctiva is then resutured to conjunctival anchor cuff 18.

If an enucleation is performed on an elective basis, a custom matched prosthetic iris could be manufactured ahead of time. To deal with emergency cases, a supply of anterior segment assemblies 24 representing a variety of iris colors could be kept on hand at the hospital to custom match the patient's natural iris. If after emergency surgery a cosmetically unsatisfactory eye color should exist in the patient, a custom-matched anterior segment assembly 24 could be manufactured and then exchanged. The anterior segment assembly exchange can be performed in a physician's office under topically applied local anesthesia.

Translucent cornea 30 may be removed by means of a suction cup. The suction cup would be fitted to translucent cornea 30 and be pulled away from the prosthetic eye 10 to remove from scleral portion 12 when a friction assembly has been utilized. In the case of a threaded anterior segment assembly 24, the suction cup would again be fitted to translucent cornea 30 and would then be twisted until anterior segment assembly 24 is removed from scleral portion 12. In both cases, a new anterior segment assembly 24 is reinserted into scleral portion 12.

Accordingly, the prosthetic eye as disclosed is constructed of a bio-compatible material which allows for a more natural and safer method of attaching the prosthesis with the extraocular muscles and the conjunctiva. Further, the method of attachment creates the biomechanics necessary to form a natural appearing and movable prosthetic eye. Finally, the presence of both biocompatible materials and proper biomechanics enable the patient to receive safe and early surgical implantation of the prosthetic eye.

It will thus be seen that the objects set forth above, among those made apparent from the preceding description are efficiently attained and, since certain changes may be made in carrying out the above method and in the construction set forth, without the departing from the spirit and scope of the invention, it is intended that all matters contained in the above description and shown in the accompanying drawings shall be interpreted as illustrative and not in a limiting sense.

It is also to be understood that the following claims are intended to cover all the generic and specific features of the invention herein described and all statements of the scope of the invention which, as a matter of language, might be said to fall therebetween.

What is claimed is:

1. A prosthetic eye for use in replacing the natural eye of a user in an eye cavity having eye muscles, comprising a spherical body having a shape and form of a natural eye, a plurality of receiving regions located on said spherical body, a plurality of tabs, attaching means for attaching said tabs to said eye muscles, inserting means for inserting said plurality of attached tabs with attached eye muscles respectively into said plurality of receiving regions to couple said muscles to said prosthetic eye, and adjusting means for permitting removal and repositioning of said tabs in said respective receiving regions without damage to said tabs or said spherical body to adjust said prosthetic eye to a natural position in said eye cavity.

2. The prosthetic eye of claim 1, wherein said spherical body is a scleral portion of said prosthetic eye.

3. The prosthetic eye of claim 2, wherein said spherical body includes an anterior segment assembly.

4. The prosthetic eye of claim 3, wherein said anterior segment assembly includes a translucent cornea, a pigmented iris and a translucent cylindrical portion matching the color, texture and pigmentation of said natural eye characteristics.

5. The prosthetic eye of claim 4, wherein said pigmented iris is painted to match the color and texture of said natural eye.

6. The prosthetic eye of claim 4, wherein said pigmented iris comprises a photograph to match the color and texture of said natural eye.

7. The prosthetic eye of claim 5, wherein said translucent cylindrical portion and said translucent cornea are molded on each end of said pigmented iris forming said anterior segment assembly.

8. The prosthetic eye of claim 6, wherein said translucent cylindrical portion and said translucent cornea are molded on each end of said pigmented iris forming said anterior segment assembly.

9. The prosthetic eye of claim 3, wherein said spherical body includes a central recess for receiving said anterior segment assembly.

10. The prosthetic eye of claim 9, wherein said anterior segment assembly attaches by means of threading said anterior segment assembly into said central recess.

11. The prosthetic eye of claim 9, wherein said central recess is surrounded by an anchor cuff recessed into said spherical body.

12. The prosthetic eye of claim 11, wherein said anchor cuff includes means for attachment to the conjunctiva of said eye cavity upon implantation of said prosthetic eye into said eye cavity to form a water-tight seal for said prosthetic eye.

13. The prosthetic eye of claim 11, wherein said anchor cuff is constructed of a porous expanded polytetrafluoroethylene.

14. The prosthetic eye of claim 11, wherein said anchor cuff is a porous material.

15. The prosthetic eye of claim 3, wherein said anterior segment assembly is constructed of polymethylmethacrylate.

16. The prosthetic eye of claim 2, wherein said scleral portion is constructed of polymethylmethacrylate.

17. The prosthetic eye of claim 2, wherein said scleral portion is constructed of silicone manufactured by injection molding techniques.

18. The prosthetic eye of claim 1, wherein said spherical body includes four receiving regions corresponding to the number of extra-ocular muscles in said natural eye.

19. The prosthetic eye of claim 18, wherein said receiving regions are oriented radially around said spherical body.

20. The prosthetic eye of claim 19, wherein said receiving regions include pairs of openings for each respectively receiving said plurality of tabs extending radially in said recesses on said spherical body.

21. The prosthetic eye of claim 1, wherein said plurality of tabs is four in number corresponding to both the number of said receiving regions and said number of said extra-ocular muscles.

22. The prosthetic eye of claim 21, wherein said tabs each have two prongs extending therefrom, said receiving regions each having a pair of openings for selectively receiving said tabs for inserting.

23. The prosthetic eye of claim 1, wherein said attaching means couples said tabs to said eye muscles.

24. The prosthetic eye of claim 1, wherein said attaching means bonds said tabs to said eye muscles.

25. The prosthetic eye of claim 1, wherein said tabs include prongs, said inserting means coupling said prongs on said tabs to said receiving regions on said spherical body.

26. The prosthetic eye of claim 15, wherein said adjusting means permits adjustment of said prongs on said tabs with respect to said receiving regions to position said prosthetic eye in relation to said natural eye.

27. The prosthetic eye of claim 1, wherein said tabs are polytetrafluoroethylene.

28. The prosthetic eye of claim 1, wherein said tabs are formed from a flat porous material.

29. The method of insertion of a prosthetic eye into an eye cavity, said prosthetic eye having a spherical body with receiving regions and an anchor cuff, and further including tabs for coupling to natural eye muscles, comprising the steps of attaching said tabs to said eye muscles, inserting said tabs with said attached eye muscles into said receiving regions and said spherical body, adjusting said tabs in said receiving regions without damage to ensure a natural positioning of said prosthetic eye, and attaching conjunctiva to said anchor cuff to provide a water tight seal.

30. The method of insertion of a prosthetic eye of claim 29, wherein attaching said tabs to said eye muscles includes suturing said eye muscles to said tabs.

31. A method of inserting a prosthetic eye of claim 30, wherein said receiving regions include openings for receiving said prongs extending radially in said recesses on said spherical body.

32. The method of insertion of a prosthetic eye of claim 31, wherein adjusting said tabs in said receiving regions includes lifting said prongs out from said openings to reinsert said prongs into other of said openings thereby readjusting the position of said prosthetic eye in said eye cavity ensuring a natural positioning prosthetic eye.

33. The method of insertion of a prosthetic eye of claim 30, wherein inserting said tabs with said attached muscles into said receiving regions includes inserting said prongs extending from said tabs into said openings in said receiving regions.

34. The method of insertion of a prosthetic eye claim 29, wherein said tabs include prongs extending therefrom for insertion into said receiving regions.

35. The method of insertion of a prosthetic eye of claim 29, wherein attaching conjunctiva to said anchor cuff includes suturing said conjunctiva to said anchor cuff creating a water tight seal.

* * * * *